(12) United States Patent
Brun et al.

(10) Patent No.: US 10,048,217 B2
(45) Date of Patent: Aug. 14, 2018

(54) CALIBRATED VOLUME DISPLACEMENT APPARATUS AND METHOD FOR DIRECT MEASUREMENT OF SPECIFIC HEAT OF A GAS

(71) Applicant: Southwest Research Institute, San Antonio, TX (US)

(72) Inventors: Klaus Brun, Helotes, TX (US); Sarah B. Simons, San Antonio, TX (US); Jeffrey A. Bennett, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 336 days.

(21) Appl. No.: 15/067,840

(22) Filed: Mar. 11, 2016

(65) Prior Publication Data

US 2017/0261448 A1    Sep. 14, 2017

(51) Int. Cl.
G01N 25/00    (2006.01)

(52) U.S. Cl.
CPC .................................. *G01N 25/005* (2013.01)

(58) Field of Classification Search
CPC .................................................... G01N 25/005
See application file for complete search history.

(56) References Cited

U.S. PATENT DOCUMENTS

| 3,095,739 | A |   | 7/1963  | Doolittle |            |
|-----------|---|---|---------|-----------|------------|
| 4,063,094 | A | * | 12/1977 | Schuman   | G01N 21/3518 |
|           |   |   |         |           | 250/336.1  |
| 5,932,793 | A |   | 8/1999  | Dayton et al. | |
| 6,065,328 | A |   | 5/2000  | Dayton et al. | |
| 6,209,387 | B1|   | 4/2001  | Savidge   | |
| 6,604,051 | B1|   | 8/2003  | Morrow et al. | |
| 6,704,660 | B2|   | 3/2004  | Morrow et al. | |
| 6,850,847 | B2|   | 2/2005  | Morrow et al. | |
| 7,197,403 | B2|   | 3/2007  | Morrow et al. | |
| 8,356,623 | B2|   | 1/2013  | Isobe et al. | |

(Continued)

FOREIGN PATENT DOCUMENTS

| DE | 19753842 C2 | 10/1999 |
| JP | 55104406 A  | 8/1980  |

(Continued)

OTHER PUBLICATIONS

Kh. Nasrifar, et al; "Prediction of Thermodynamic Properties of Natural Gas Mixtures Using 10 Equations of State Including a New Cubic Two-constant Equation of State"; Journal of Petroleum Science & Engineering 51 pp. 253-266 (2006).

(Continued)

*Primary Examiner* — Mamadou Diallo
(74) *Attorney, Agent, or Firm* — Grossman, Tucker et al

(57) ABSTRACT

A method and apparatus for the direct measurement of specific heat at constant pressure (Cp). A control fluid of a known amount is supplied to a near adiabatic test chamber having a volume. A collapsible bladder within the test chamber is inflated with an incompressible fluid, changing the volume of the test chamber. The change in pressure and temperature of the control fluid relative to the change in volume of the test chamber is measured. The steps are repeated with a sample fluid. The isentropic enthalpy and specific heat at constant pressure of the sample fluid is determined.

20 Claims, 2 Drawing Sheets

(56) References Cited

U.S. PATENT DOCUMENTS

2010/0163119 A1 7/2010 Isobe et al.
2016/0312776 A1* 10/2016 Yagi .................... F04D 15/0044

FOREIGN PATENT DOCUMENTS

| JP | 5747723 B2 | 10/1982 |
|----|------------|---------|
| JP | 58115356 A | 7/1983 |
| JP | 58115357 A | 7/1983 |
| JP | 60129618 A | 7/1985 |
| JP | 60129642 A | 7/1985 |
| JP | 2010091320 A | 4/2010 |
| JP | 2010169657 A | 8/2010 |
| JP | 4705140 B2 | 6/2011 |
| WO | 1988006291 A1 | 8/1988 |

OTHER PUBLICATIONS

P. Rasmussen, et al; "Centrifugal Compressor Applications—Upsteam and Midstream" (18 pgs); <<http://turbolab.tamu.edu/proc/turboproc/T38/ch16_Rasmussen.pdf>> (accessed Jan. 27, 2016).

* cited by examiner

CALIBRATED VOLUME DISPLACEMENT APPARATUS AND METHOD FOR DIRECT MEASUREMENT OF SPECIFIC HEAT OF A GAS

FIELD

The present disclosure is directed to an apparatus and method for the direct measurement of specific heat at constant pressure of a fluid through calibrated volume displacement.

BACKGROUND

Determination of enthalpy and specific heat at constant pressure (Cp) of process gasses or gas mixtures is relatively important in various applications. Sizing of machinery relies, in part, upon the accuracy of thermodynamic properties of the process gasses and, in particular, relies upon the accuracy of the specific heat. For example, in the turbomachinery industry, compressor manufacturers use enthalpy to determine, for example, the power requirement and isentropic head of the compressor. Enthalpy may be calculated from specific heat at constant pressure using the following equation:

$$h = C_p(T,P)\Delta T \qquad \text{Equation 1:}$$

wherein h is enthalpy, $C_p$ is specific heat at constant pressure, T is temperature and P is pressure. Specific heat at constant pressure (Cp), is typically calculated from measurements of specific heat at constant volume ($C_v$) and speed of sound (SoS) measurements. Determination of specific heat at constant pressure (Cp) by indirectly calculating from specific heat at constant volume ($C_v$) and speed of sound measurements (SoS), may introduce relatively significant error.

In general, thermodynamic properties are calculated using a pure gas component model matched within 1% of actual pure gas experimental data. Properties of gas mixtures, more common for industrial applications, are computed using mixing laws applied in various equations of state (EoS) models. These calculations may introduce relatively significant error when calculating enthalpy. In one example, Kh. Nasrifar and O. Bolland report a 2.5% deviation for speed of sound (SoS) values for natural gas mixtures when using commonly available equation of state models. *Prediction of Thermodynamic Properties of Natural Gas Mixtures Using 10 Equations of State Including New Cubic Two Constant Equations of State,* 51 J. Petroleum Sc.& Eng'g 253 (2006). Further, measurement of errors of up to 0.5% are typically seen when directly measuring $C_v$ and SoS of gas mixtures to obtain relatively more accurate results for a particular fluid of interest.

Direct measurement of specific heat at constant pressure may involve the use of an enclosure filled with a known mass of the sample fluid at a certain temperature and pressure. The volume of the enclosure is varied, such as by way of a piston. Changes of volume are applied at relatively slow rates, taking 1 second or more, to change the volume of the sample fluid. However, the efficiency of the process is less than 100% and the slow rate of change in the volume results in a loss of heat to the environment altering the temperature values and reducing the accuracy of the calculation.

Accordingly, room remains for improvement in the accuracy of determining specific heat at constant pressure for gas and gas mixtures and particularly for non-ideal gas mixtures. Improvements in accuracy may then allow for improvements in a number of aspects of process and machine design, including sizing and material selection.

SUMMARY

An aspect of the present disclosure is directed to a method for the direct measurement of specific heat at constant pressure (Cp). The method includes supplying a control fluid of a known amount to a test chamber having a volume, wherein the test chamber exhibits less than 1% heat loss of the total energy input. A collapsible bladder is inflated with an incompressible fluid to change the volume of the test chamber. The change in pressure and the change in temperature of the control fluid are measured relative to the change in the volume of the test chamber as the collapsible bladder is inflated. The actual change in enthalpy of the control fluid and a process efficiency parameter are calculated.

A sample fluid of a known amount is supplied to the test chamber. The collapsible bladder is inflated with the incompressible fluid to change the volume of the test chamber. The change in pressure and the change in temperature of the sample fluid are measured relative to the change in the volume of the test chamber as the collapsible bladder is inflated. The change in isentropic enthalpy of the sample fluid is determined based on 1) the change in pressure of the sample fluid measured relative to the change in volume, 2) the known amount of the sample fluid, and 3) the process efficiency parameter. In addition, the specific heat at constant pressure of the sample fluid is determined based on the change in temperature of the sample fluid measured and the change in isentropic enthalpy of the sample fluid.

In another aspect, the present disclosure is directed to an apparatus for the direct measurement of specific heat at constant pressure (Cp). The apparatus includes a test chamber, wherein the test chamber exhibits less than 1% of heat loss of the total energy input, and a collapsible bladder positioned within the test chamber. The apparatus further includes a reservoir for incompressible fluid in fluid communication with the collapsible bladder, a pump operatively coupled to the reservoir configured to displace the incompressible fluid into the collapsible bladder, and a fluid supply system including one or more sample fluid reservoirs coupled to the test chamber by a first flow path. In addition instrumentation, including a pressure sensor and a temperature sensor, is operatively coupled to the test chamber.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
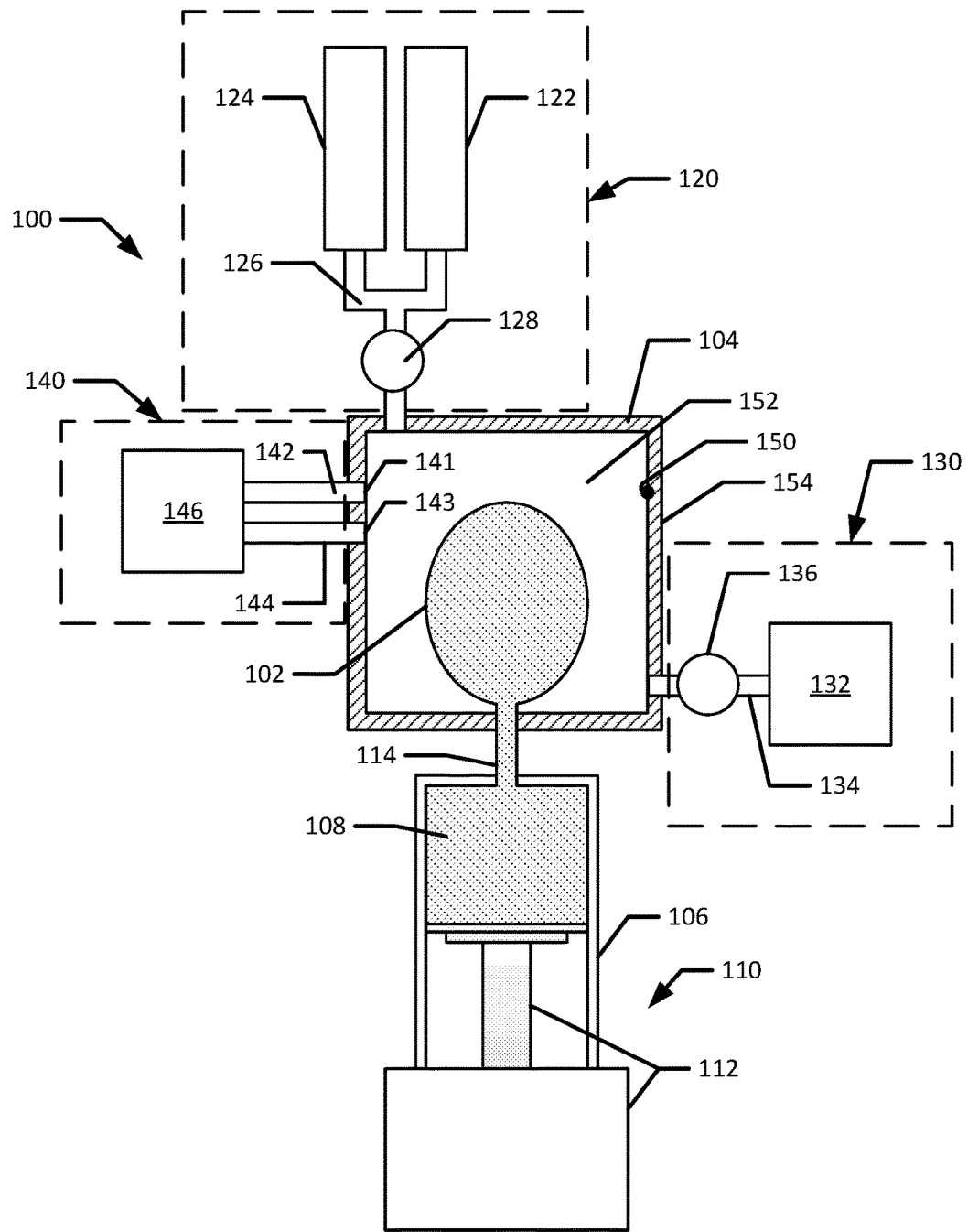
FIG. 1 illustrates a schematic diagram of an exemplary embodiment of an apparatus contemplated herein.

In process and machinery design, factors such as required power and isentropic fluid dynamic efficiency cannot be calculated without identifying the specific heat at constant pressure of the process fluid. In the case of a centrifugal compressor, for example, power and efficiency are determined by the below equations.

$$\text{Actual Power} = \dot{m}\Delta h_{Actual} = \dot{m}C_P(T_{Exit} - T_{Inlet}) \quad \text{Equation 2}$$

$$\text{Isentropic Power} = \dot{m}\Delta h_{Isentropic} = \dot{m}C_P T_{Inlet}\left[\left(\frac{P_{Exit}}{P_{Inlet}}\right)^{\frac{k-1}{k}} - 1\right] \quad \text{Equation 3}$$

$$\eta_{Isentropic} = \frac{\text{Isentropic Power}}{\text{Actual Power}} \quad \text{Equation 4}$$

Equations 2 through 4, above, rely upon knowing the specific heat at constant pressure $C_p$ of the process fluid. Centrifugal compressors are commonly employed in gas turbines, turbochargers and superchargers, pipelines, refinery and chemical plant compressors for moving natural gas and other fluids, water chillers, pneumatics, and in the manufacture of purified end product gasses. Expanders are often used in conjunction with compressors, such as for driving the compressors. The margin of error in calculating specific heat at constant pressure $C_p$ using common equations of state (EoS) may be significant enough to lead to errors in machine sizing, process operating map deviations, and errors in discharge temperature calculations, leading to poor material selection.

The present disclosure is directed to an apparatus and method for the direct measurement of specific heat at constant pressure of a fluid through calibrated volume displacement, resulting in temperature and pressure changes in the fluid. The apparatus applies a calibrated amount of work to a known mass (or volume) of fluid while monitoring the changes in temperature and pressure. The work is applied in less than 1 second and preferably in the range of 0.01 seconds to 0.2 seconds. A control fluid with aerodynamic similitude to the sample fluid is tested in the apparatus to determine a process efficiency parameter, which is indicative of energy losses in the testing apparatus and method. The process efficiency parameter is then used to calculate enthalpy and specific heat at constant pressure of the sample fluid. As understood herein, a fluid may be understood as a substance, such as a gas or gas mixture, which is capable of flowing and is capable of changing shape at a steady rate when enacted upon by a force. The apparatus and method are particularly applicable to the measurement of non-ideal gas mixtures, which deviate from ideal gas behavior.

Table 1 provides a reference to the nomenclature utilized herein.

TABLE 1

| Nomenclature | |
| --- | --- |
| Symbol | Variable |
| $C_p$ | Specific heat at constant pressure |
| $C_v$ | Specific heat at constant volume |
| h | Enthalpy |
| $\Delta h_{actual}$ | Actual change in actual enthalpy |
| $\Delta h_{Isentropic}$ | Change in isentropic enthalpy |
| L | Characteristic linear dimension |
| m | Mass of the gas |
| M | Molar mass of the gas |
| P | Pressure |
| $\Delta P$ | Change in Pressure |
| R | Universal gas constant |
| Re | Reynold's number |
| SoS | Speed of Sound |
| T | Temperature |

TABLE 1-continued

| Nomenclature | |
| --- | --- |
| Symbol | Variable |
| $\Delta T$ | Change in Temperature |
| v | Velocity |
| V | Volume |
| $\Delta V$ | Change in Volume |
| W | Work |
| γ | Ratio of specific heats |
| η | Efficiency |
| ρ | Density |
| μ | Dynamic Viscosity |
| ν | Kinematic Viscosity |

Generally, the enthalpy, h, of a fluid is defined as the energy or work required in an open system to transition from one temperature and pressure condition to another. The change in enthalpy, $\Delta h$, is equal to the change in the internal energy of the system, plus the pressure-volume work that the system has done on its surroundings. Enthalpy, in terms of specific heat at constant pressure, is typically calculated using Equation 1, reproduced again below for convenience.

$$h = C_p(T,P)\Delta T \quad \text{Equation 1:}$$

wherein h is enthalpy, Cp is heat capacity at constant pressure, T is temperature and P is pressure. Isentropic enthalpy, $h_{Isentropic}$, is understood as the enthalpy that would be achieved under idealized circumstances (i.e., an adiabatic process), whereas actual enthalpy, $h_{Actual}$, is understood as the enthalpy that is actually measured. The difference between isentropic enthalpy and actual enthalpy is due to, for example, a degradation of the energy in the process, such as the dissipation of heat or frictional losses. Understanding enthalpy, h, and, particularly change in enthalpy, $\Delta h$, is a relatively important factor when designing a process and corresponding machinery that applies work to a fluid.

The testing apparatus contemplated herein is illustrated in FIG. 1. The testing apparatus 100 includes a collapsible bladder 102 that is situated within a well-insulated, near adiabatic, chamber 104. The bladder 102 is in fluid communication with a reservoir 106, which has an incompressible fluid 108 contained therein. A pump 110, such as a piston and a piston actuator 112, is operatively coupled to the reservoir 106 and displaces the incompressible fluid 108 from the reservoir 106 into the bladder 102 through flow path 114. Operatively coupling refers to herein the association of the reservoir and the pump in such a manner that the pump may act upon (apply forces upon) the fluid contained within the reservoir. In the illustrated example, the piston is positioned within the reservoir and pushes the incompressible fluid from the reservoir into the bladder 102. Other pumps may alternatively be utilized to move the incompressible fluid from the reservoir 106 to the collapsible bladder 102.

A sample supply system 120 is in fluid communication with the test chamber 104. The sample supply system 120 includes at least one reservoir, such as a gas or liquid cylinder, for the fluid under investigation (i.e., the sample fluid) 122 and at least one reservoir, such as a gas or liquid cylinder, for the control fluid 124. The control fluid is understood herein as a fluid that has a known isentropic enthalpy and a known specific heat at constant pressure ($C_p$). The sample fluid and control fluid reservoirs are coupled to the test chamber 104 through flow path 126, which may include one or more devices 128 to control the pressure, mass, and temperature of the fluid introduced into the test chamber 104, such devices 128 include, for example, mass flow controllers, pressure regulators, thermal regulators or combinations thereof.

Further, a vacuum system 130 is optionally provided to remove fluid present in the test chamber 104. The vacuum system 130 includes one or more vacuum pumps 132 connected to the test chamber 104 through a flow path 134. The flow path 134 may include one or more flow control devices 136, such as a shut off valve, to prevent fluid escaping the test chamber 104 during testing.

In addition, instrumentation 140 for measuring pressure and temperature is operatively coupled to the testing chamber 104, either directly being mounted to the chamber 104 or indirectly mounted in the test fluid supply system 120. Operative coupling of the instrumentation is understood as mounting the instrumentation to the test chamber 104 in a manner that allows for the instrumentation to measure process variable such as temperature and pressure of the fluid in the test chamber 104. In embodiments, instrumentation includes temperature and pressure sensors 142, 144 as well as one or more data processing systems 146 configured to capture and output the instrumentation data provided by the sensors. Preferably, the instrumentation is mounted in the test chamber 104 through openings 141, 143. Suitable outputs may include displays, printouts, memory devices such as a memory drive or disc, etc.

In embodiments, the collapsible bladder 102 is formed from materials that exhibit flexibility, relatively low strain at operating pressures, and, preferably, relatively low thermal conductivity at operating temperatures. The exhibited strain by the bladder material is preferably 5% or less and more preferably 3% or less and more preferably 1% or less when measured according to ASTM D638-14 or ASTM D412-15a (Test Method A) at 20° C. Further, the bladder material preferably exhibits a thermal conductivity of 0.5 $Wm^{-1}K^{-1}$ or less, and more preferably 0.3 $Wm^{-1}K^{-1}$ or less, including values and ranges between 0.01 $Wm^{-1}K^{-1}$ to 0.5 $Wm^{-1}K^{-1}$ as measured at 20° C. The collapsible bladder may be formed from rubber or a thermoplastic material.

The test chamber 104 defines an interior volume 152, has an interior surface 150 and has an exterior surface 154. The chamber 104 is near adiabatic and exhibits less than 1% of heat loss of the total energy input, including gains or losses in heat that may be transferred to or from the chamber and external environment. Preferably, the test chamber 104 exhibits a thermal conductivity of 0.5 $Wm^{-1}K^{-1}$ or less, and preferably 0.3 $Wm^{-1}K^{-1}$ or less, including values and ranges between 0.01 $Wm^{-1}K^{-1}$ to 0.5 $Wm^{-1}K^{-1}$ as measured at 20° C. In embodiments, the chamber wall is formed of monolithic structures, such as ceramic materials, metals, or metal alloys. In preferred embodiments, a thermal barrier coating is deposited on the interior surface 150 of the chamber, which may be formed of the above mentioned monolithic materials. The thermal barrier coating includes ceramic coatings such as YSZ, mullite, alumina, CeO2/YSZ, rare-earth zirconates, rare earth oxides, and combinations thereof; metal-glass composites; and combinations of ceramic coatings and metal-glass composites. The thickness of the thermal barrier coating is preferably in the range of 0.1 mm to 4 mm, including all values and ranges therein, and more preferably in the range of 1 mm to 2 mm. In addition, the exterior of the chamber 154 is preferably covered in a layer of insulation, such as ceramic fibers, mica-resin laminates, glass based materials, and resin based materials such as NOMEX available from DUPONT DE NEMOURS.

The incompressible fluid 108 is understood herein as a fluid in which the density of the fluid remains constant upon the application of pressure. The incompressible fluid preferably exhibits a bulk modulus in the range of $1\times10^9$ Pa or greater, such as in the range of $1\times10^9$ Pa to $1\times10^{11}$ Pa, including all values and ranges therein, at 20° C. The incompressible fluid also preferably exhibits a dynamic viscosity in the range of $1\times10^1$ mPa*s to $1\times10^3$ mPa*s, including all values and ranges therein, at 20° C. Exemplary incompressible fluids include water, mineral oil, glycol, organophosphate ester, polyalphaolefin, propylene glycol, and silicone oils. The piston 110 and piston actuator 112 may be operated by hydraulics, pneumatics or electrically, depending on the desired rates and forces required.

The flow paths 114, 126, and 134 described herein are, in embodiments, formed from pipes or tubing, and provide fluid communication to and from the testing chamber. The flow paths, and particularly the flow path of the fluid supply system 124, preferably exhibits a thermal conductivity of a thermal conductivity of 0.5 $Wm^{-1}K^{-1}$ or less, and preferably 0.3 $Wm^{-1}K^{-1}$ or less, including values and ranges between 0.01 $Wm^{-1}K^{-1}$ to 0.5 $Wm^{-1}K^{-1}$ as measured at 20° C. The material forming the flow paths may be formed from, for example, a polymer material, a ceramic material, a metal or metal alloy, and combinations thereof.

In operating the testing apparatus, the method of testing preferably includes running at least two tests. The first test, being a calibration test, utilizes a control fluid that has a known isentropic enthalpy and exhibits an aerodynamic similitude to the sample fluid of interest. Process efficiency is calculated from the control fluid so that work performed on the control and sample fluids by the testing apparatus may be determined. The second test utilizes the sample fluid of interest, which again may include, for example, a gas or mixtures of gasses and, in particular, non-ideal gas mixtures. It should be appreciated that the order of testing the control fluid and sample fluid may be rearranged such that the sample fluid may be run in the first test and the control fluid may be run in the second test. It should also be appreciated that more than one sample fluid may be examined relative to a control fluid test. That is, one control fluid may be examined in the testing device to determine the process efficiency parameter and a number of sample fluids with aerodynamic similitude to the control fluid may be tested and the specific heat at constant pressure ($C_p$) may be calculated based on the process efficiency parameter of the one control fluid. However, in preferred embodiments, each sample fluid test is either preceded or followed by a control fluid test.

The measure of aerodynamic similitude of interest herein is the Reynolds number (Re) of the test and control fluids, which is defined as follows:

$$Re \equiv \frac{\rho v L}{\mu}, \qquad \text{Equation 5}$$

wherein ρ is the density of the fluid, μ is the dynamic viscosity of the fluid, v is the maximum velocity of the object relative to the fluid, and L is a characteristic linear dimension, (traveled length of the fluid). Given that the v and L remain constant between the sample fluid and control fluid, appropriate control fluids may be chosen based on a comparison of the ratios of the density to dynamic viscosities of the control and sample fluids, which may be expressed as the ratio of the kinematic viscosities of the fluids, defined as follows.

$$\frac{\frac{\rho_s}{\mu_s}}{\frac{\rho_c}{\mu_c}} = \frac{v_s}{v_c}, \quad \text{Equation 6}$$

wherein $\rho_s$ is the density of the sample fluid, $\mu_s$ is the dynamic viscosity of the sample fluid, and $v_s$ is the kinematic viscosity of the sample fluid and $\rho_c$ is the density of the control fluid, $\mu_c$ is the dynamic viscosity of the control fluid, and $v_c$ is the kinematic viscosity of the control fluid. Preferably, the ratio of the kinematic viscosity is within 0.5 to 1.5, including all values and ranges therein. Non-limiting examples of calibration gasses include nitrogen or carbon dioxide.

Figure 2:
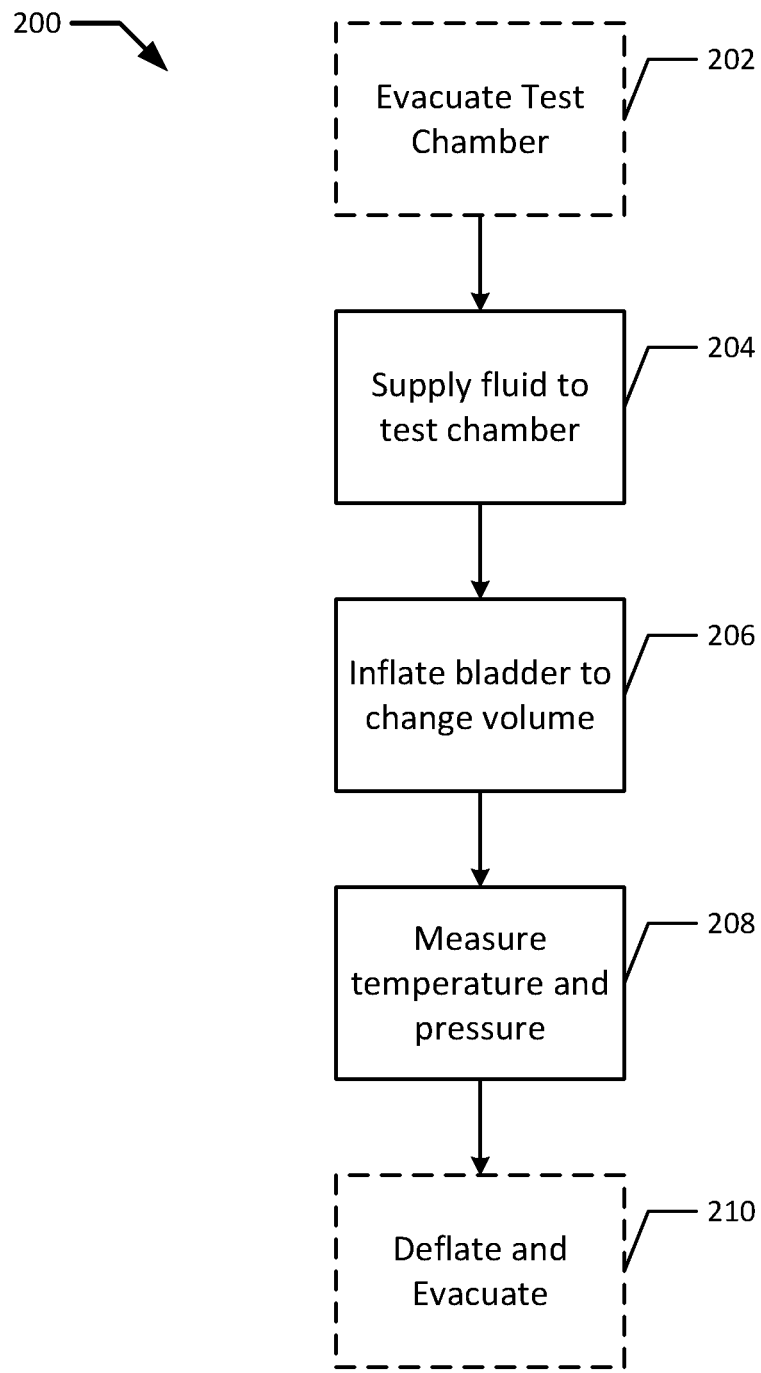
FIG. 2 illustrates a flow diagram of an exemplary embodiment of a method of testing.

One embodiment of a test method 200, illustrated in FIG. 2, optionally begins with the evacuation 202 of any fluid present in the testing chamber 104 through the vacuum system 130. The testing chamber 104 is evacuated to $1\times10^{-9}$ to $1\times10^{1}$ mTorr, including all values and ranges therein. Once evacuated, the test chamber 104 is then filled 204 with a known amount (mass or volume) of the fluid to be tested (either control or sample fluid) at known temperature and pressure from the fluid supply system 120. The amount of fluid entering the test chamber 104 being determined by, for example, the mass flow controller and the temperature and pressure being determined by, for example, instrumentation 140.

Once the fluid to be tested is supplied to the test chamber 104, the pump 110 is actuated 206 and forces incompressible fluid 108 into the collapsible bladder 102, which rapidly expands due to the increasing volume of incompressible fluid 108. The incompressible fluid 108 is transferred to the collapsible bladder 102 altering the volume 152 that the test fluid occupies within the test chamber. During expansion of the bladder, changes in temperature and pressure are monitored 208 relative to the change in volume using the temperature and pressure sensors 142, 144 and the sensor output is received by the data processing system 146. In preferred embodiments, expansion of the bladder occurs in less than 1 second and more preferably in the range of 0.01 s to 0.2 seconds. The collapsible bladder may then be deflated 210 and the test chamber is optionally evacuated if additional testing is performed and the method repeated. Testing conditions, such as volumetric flow rate of the incompressible fluid and the total change in volume within the test chamber, are maintained the same between the sample fluids and control fluids.

As noted above, the test may begin with either the control fluid or the sample fluid. Additionally or alternatively, once a control fluid is tested and the efficiency is known for that fluid, it need not be re-tested and just one or more sample fluids of aerodynamic similitude may be introduced into the system. Further, a database of control fluids may be developed and, overtime, the efficiency values may be recalibrated due to changes in the test apparatus, such as the strain exhibited by the collapsible balloon or changes in the incompressible fluid over time.

Once the control fluid has been tested, the change in actual enthalpy is understood by combining the following equations using the pressures and temperatures measured relative to the change in volume captured while testing the control fluid.

$$W = \Delta h_{actual} \cdot m = \int P(V)dV \quad \text{Equation 7}$$

$$\Delta h_{actual} = \frac{\int P(V)dV}{m} = C_p \cdot \Delta T \quad \text{Equation 8}$$

wherein $\Delta_{Actual}$ is the actual change in enthalpy of the control fluid, m is the mass of the control fluid in the test chamber, P is the measured pressure of the control fluid in the test chamber, V is the known volume of the control fluid in the test chamber, T is the measured temperature of the control fluid in the test chamber and $C_p$ is the specific heat at constant volume. Once the actual enthalpy is known for the control fluid based on Equation 8, the efficiency of the apparatus may be calculated using the known isentropic enthalpy of the control fluid according to Equation 9 below.

$$\eta_{Isentropic} \equiv \frac{\Delta h_{Isentropic}}{\Delta h_{Actual}} \quad \text{Equation 9}$$

wherein $\eta_{Isentropic}$ is the process efficiency parameter, $\Delta h_{Isentropic}$ is the change in isentropic enthalpy of the control fluid, and $\Delta h_{Actual}$ is the change in actual enthalpy of the control fluid.

The process efficiency parameter, $\eta_{Isentropic}$, may then be used in determining the specific heat at constant pressure for the sample fluid according to the equations below.

$$\frac{\int P(V)dV}{m} \times \eta_{Isentropic} = \Delta h_{Isentropic}, \quad \text{Equation 10}$$

$$C_p = \frac{\Delta h_{Isentropic}}{\Delta T} \quad \text{Equation 11}$$

wherein, P is the measured pressure of the sample fluid, V is the known volume of the test chamber, m is the mass of the sample fluid in the test chamber, $\eta_{Isentropic}$ is the process efficiency parameter, $\Delta h_{Isentropic}$ is the isentropic enthalpy and T is the measured temperature of the sample fluid.

The apparatus and method herein provides a direct measurement of specific heat at constant pressure in an attempt to reduce error generated by indirect determination of specific heat at constant pressure through equations of state or by direct determination of specific heat at constant pressure using non-adiabatic processes. The apparatus and method are particularly useful in determining the specific heat at constant pressure of non-ideal gas mixtures. The reduction in error then allows for more accurate process and machine design calculations. In particular, it is contemplated that machine sizing will be improved with more accurate calculations of the required work that can be performed. Further, fluid dynamic efficiency values would have a relatively smaller margin of error, thus increasing the ability to more precisely describe the range of operation.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

The invention claimed is:

1. A method for the direct measurement of specific heat at constant pressure (Cp), comprising:

supplying a control fluid of a known amount to a test chamber having a volume, wherein said test chamber exhibits less than 1% heat loss of the total energy input;

inflating a collapsible bladder with an incompressible fluid to change the volume of said test chamber and measuring a change in pressure and a change in temperature of said control fluid relative to said change in said volume of said test chamber as said collapsible bladder is inflated;

calculating the actual change in enthalpy of said control fluid and calculating a process efficiency parameter;

supplying a sample fluid of a known amount to said test chamber;

inflating said collapsible bladder with said incompressible fluid to change the volume of said test chamber and measuring a change in pressure and a change in temperature of said sample fluid relative to said change in said volume of said test chamber as said collapsible bladder is inflated;

determining a change in isentropic enthalpy of said sample fluid based on 1) said change in pressure of said sample fluid measured relative to said change in volume, 2) said known amount of said sample fluid, and 3) said process efficiency parameter; and determining the specific heat at constant pressure of said sample fluid based on said change in temperature of said sample fluid measured and said change in isentropic enthalpy of said sample fluid.

2. The method of claim 1, wherein said change in isentropic enthalpy of said sample fluid, $\Delta h_{Isentropic}$, is determined using the following equation:

$$\frac{\int P(V)dV}{m} \times \eta_{Isentropic} = \Delta h_{Isentropic}$$

wherein P is pressure, V is volume, m is mass, $\eta_{Isentropic}$ is the process efficiency parameter.

3. The method of claim 1, wherein said specific heat at constant pressure of said sample fluid is determined using the following equation:

$$C_p = \frac{\Delta h_{Isentropic}}{\Delta T}$$

wherein Cp is the specific heat at constant pressure of said sample fluid, $h_{isentropic}$ is isentropic enthalpy of said sample fluid, and $\Delta T$ is said change in temperature of said sample fluid.

4. The method of claim 1, wherein said control fluid exhibits an aerodynamic similitude to said sample fluid and has a known change in isentropic enthalpy $\Delta h_{Isentropic}$.

5. The method of claim 4, wherein said aerodynamic similitude is determined by the ratio of the kinematic viscosity of the sample fluid, $\upsilon_s$, to the kinematic viscosity of the control fluid, $\upsilon_c$.

6. The method of claim 5, wherein the ratio of $$\frac{\upsilon_s}{\upsilon_c}$$

is in the range of 0.5 to 1.5.

7. The method of claim 1, wherein said actual change in enthalpy of said control fluid is calculating according to the following equation:

$$\Delta h_{actual} = \frac{\int P(V)dV}{m} = C_p \cdot \Delta T$$

wherein P is pressure, V is volume, m is mass, $C_p$ is specific heat capacity of the control fluid and $\Delta T$ is said change in temperature of said control fluid.

8. The method of claim 1, wherein said process efficiency parameter is calculated according to the following equation:

$$\eta_{Isentropic} \equiv \frac{\Delta h_{Isentropic}}{\Delta h_{Actual}}$$

wherein $\eta_{Isentropic}$ is the process efficiency parameter of said control fluid, $h_{Isentropic}$ is the isentropic enthalpy of said control fluid and $h_{Actual}$ is the actual enthalpy of said control fluid.

9. The method of claim 1, wherein said control fluid is selected from nitrogen and carbon dioxide.

10. The method of claim 1, wherein said sample fluid is a non-ideal gas mixture.

11. The method of claim 1, further comprising evacuating said test chamber prior to supplying said sample fluid to said test chamber.

12. The method of claim 1, further comprising displacing said incompressible fluid from a reservoir into said collapsible bladder with a pump.

13. An apparatus for the direct measurement of specific heat at constant pressure (Cp), comprising:
   a test chamber, wherein said test chamber exhibits less than 1% heat loss of the total energy input;
   a collapsible bladder positioned within said test chamber;
   a reservoir for incompressible fluid in fluid communication with said collapsible bladder;
   a pump operatively coupled to said reservoir configured to displace the incompressible fluid into said collapsible bladder;
   a fluid supply system including one or more sample fluid reservoirs coupled to said test chamber by a first flow path; and
   instrumentation, including a pressure sensor and a temperature sensor, operatively coupled to said test chamber.

14. The apparatus of claim 13, wherein said pump comprises a piston and piston actuator.

15. The apparatus of claim 13, wherein said fluid supply system further comprising a control fluid reservoir.

16. The apparatus of claim 13, wherein said control fluid reservoir contains a control gas selected from nitrogen or carbon dioxide.

17. The apparatus of claim 13, wherein said fluid supply system further comprises a mass flow controller.

18. The apparatus of claim 13, further comprising a vacuum system coupled to said test chamber by a second flow path.

19. The apparatus of claim 13, wherein said test chamber includes an interior surface including a thermal barrier coating deposited on said interior surface.

20. The apparatus of claim 13, wherein said test chamber includes an exterior surface including a layer of insulation covering said exterior surface.

* * * * *